United States Patent [19]

Yu et al.

[11] Patent Number: 5,420,036

[45] Date of Patent: May 30, 1995

[54] BACILLUS POLYMYXA 1 CAPABLE OF PRODUCING POLYSACCHARIDES AND POLYSACCHARIDES PRODUCED BY THIS STRAIN

[75] Inventors: Ju H. Yu, 397-35, Hongeun-3-dong, Seodaemoon-gu; Yong M. Shin; Kyu S. Rhee, all of Seoul, Rep. of Korea

[73] Assignees: Haitai Confectionery Co., Ltd.; Ju H. Yu, both of Seoul, Rep. of Korea

[21] Appl. No.: 47,073

[22] Filed: Apr. 16, 1993

Related U.S. Application Data

[63] Continuation of Ser. No. 776,857, Oct. 16, 1991, abandoned, which is a continuation of Ser. No. 592,019, Oct. 20, 1990, abandoned.

[30] Foreign Application Priority Data

Oct. 4, 1989 [KR] Rep. of Korea .................... 89-14213

[51] Int. Cl.$^6$ .............................................. C12N 1/20
[52] U.S. Cl. ................................. 435/252.5; 435/832; 435/838; 435/101
[58] Field of Search ....................... 435/252.5, 832, 838

[56] References Cited

U.S. PATENT DOCUMENTS

| | | | |
|---|---|---|---|
| 2,821,501 | 1/1958 | Simpson | 435/99 |
| 3,812,012 | 5/1974 | Buschmann et al. | 435/252.5 |
| 3,923,978 | 12/1975 | Kaskahima et al. | 424/118 |
| 3,930,954 | 1/1976 | Irie | 435/240.2 |
| 3,940,479 | 2/1976 | Shomura et al. | 424/118 |

FOREIGN PATENT DOCUMENTS 285829 10/1988 European Pat. Off. .

OTHER PUBLICATIONS

Smith, Nathan R. et al., Agr. Monograph 16, U.S. Dept. of Agriculture, pp. 97–100 (1952).
Biswas, Chatra et al., J. Biol. Chem., 245: 4900–4906 (1970).
Wyman, Arlene et al., J. Biol. Chem., 250: 3897–3903 (1975).
Stansly, P. G. et al., J. Bacteriology, 54: 549–556 (1947).
Sandford, Adv. in Carbhyd. Chem. and Biochem., vol. 36, pp. 265,274 and 300.
Gherna et al., ATCC Catalogue of Bacteria and Phages, 1989, p. 30.
Bergey's Manual of Systematic Bacteriology, vol. 2, pp. 1105–1121, 1123–1127 and 1134.

Primary Examiner—Johnnie R. Brown
Assistant Examiner—Pamela S. Webber
Attorney, Agent, or Firm—Finnegan, Henderson, Farabow, Garrett & Dunner

[57] ABSTRACT

The present invention relates to Bacillus polymyxa Haitai 1 (KCCM-10001) capable of producing polysaccharides which are viscous and thermally stable, and have the capacities of water holding, film forming and emulsifying, and can reversibly form a gel when heated, and to polysaccharides having the above characteristics which are produced by utilizing the said microorganism.

2 Claims, 5 Drawing Sheets

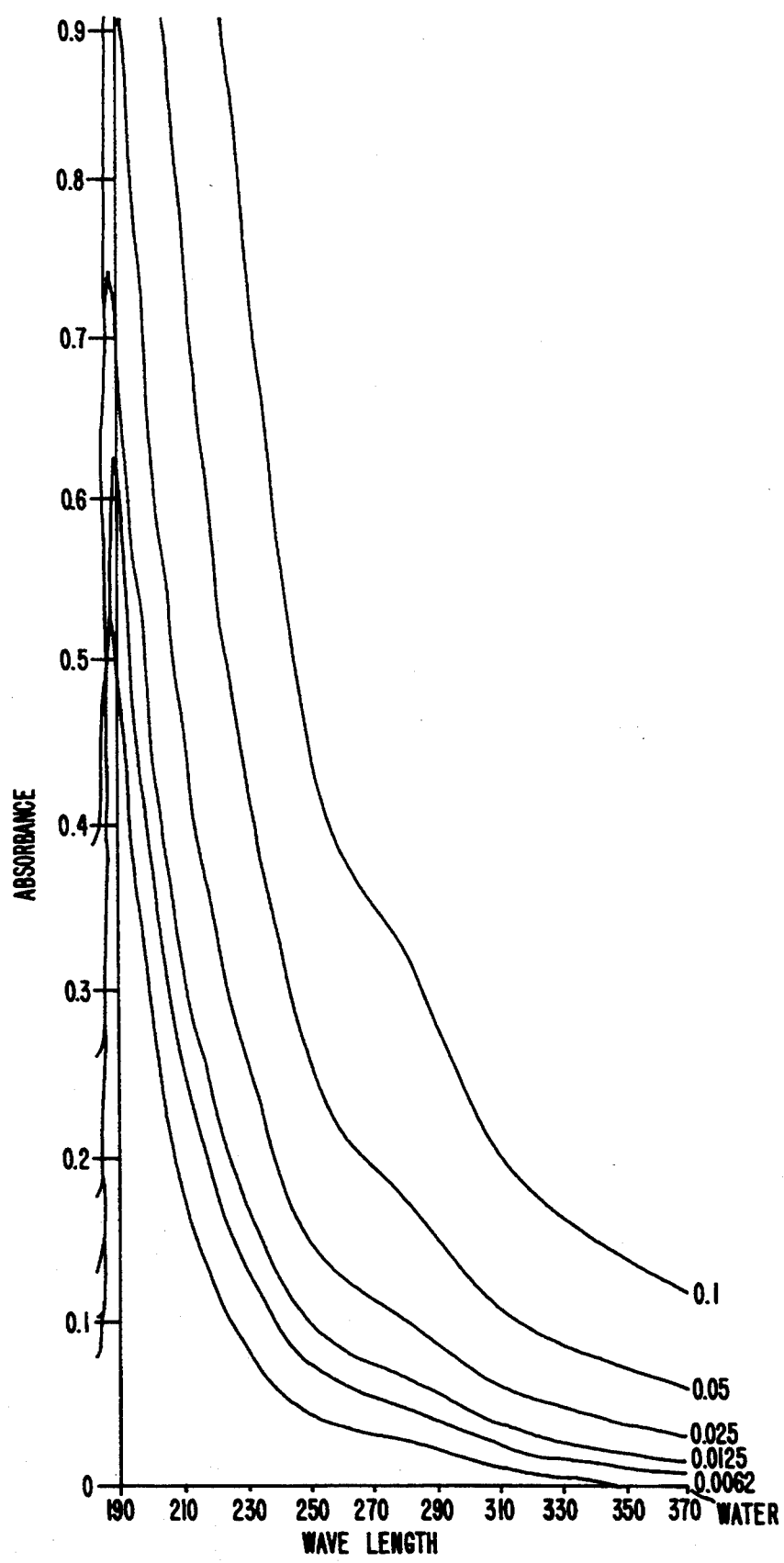
F I G. 2

BACILLUS POLYMYXA 1 CAPABLE OF PRODUCING POLYSACCHARIDES AND POLYSACCHARIDES PRODUCED BY THIS STRAIN

This application is a continuation of application Ser. No. 07/776,857, filed Oct. 16, 1991, now abandoned, which is a continuation of application Ser. No. 07/592,019, filed Oct. 2, 1990, now abandoned.

FIELD OF THE INVENTION

The present invention relates to *Bacillus polymyxa* Haitai 1 strains capable of producing polysaccharides which have thermal stability and can reversibly form a gel by heat and polysaccharides having the above characteristics produced by these strains. *Bacillus polymyxa* Haitai 1 has been deposited with the international depository named "Korean Culture Center of Microorganisms" with the Accession No. of KCCM-10001 dated Jul. 1, 1990.

BACKGROUND OF THE INVENTION

Polysaccharides form a significant part of the market of aqueous polymers and have been developed for industrial applications because of their various functional properties. These polysaccharides are present in leaves, stems and roots of plants, seaweeds, animals, microorganisms, mycelia, insect chitins and the like. Natural polysaccharides extracted from plants and seaweeds were most applicable so far. As an example of these polysaccharides, starch of various plants, locust bean gum and guar gum extracted from roots of plants, agar, alginate extracted from seaweeds, and pectin extracted from plants may be mentioned (Whistler, R. L.: Industrial gums, Academic Press, New York (1959)). The quantity and the quality of the natural polysaccharides extracted from the plants greatly depend on the climate of the year. Thus, the costs, quality and supply of these polysaccharides are irregular, and the continuously increasing consumption of natural polysaccharides is not satisfied (Sandford, P.A.: *Polysaccharides in Food* (Blanshard, J. M. V. and Gaylord, N. G. ed) 8, 693–711 (1968)). Therefore, polysaccharides produced by microorganisms have been needed in order to overcome these problems.

Polysaccharides produced by microorganisms are of three types:
a. Exocellular polysaccharides of microorganisms in the form of a capsule or slime,
b. Endocellular polysaccharides of microorganisms as an energy stock material in the microorganisms, and
c. Polysaccharides constituting the cell wall.

Recently, due to the commercial success of dextran and xanthan gum among polysaccharides produced by microorganisms, the preparation of polysaccharides by microorganisms has become of increasing interest. Polysaccharides produced by microorganisms have the functional characteristics such as an emulsifying capacity, a viscosity increasing capacity, the capacities of stability and gelation, a water holding capacity, a film forming capacity, physiological activating capacity, an aggregation capacity, and the like. Therefore, investigations for various uses in the field of foods, cosmetics, oils and medicines have been conducted. Such uses are based on the inherent properties of polysaccharides. When the polysaccharides are produced by the fermentation of microorganisms, they have numerous advantages such as control of the quantity and the quality, control of the degree of synthesis by controlling the fermentation conditions, easy availability of cheap and plentiful raw materials, productivity with a high yield by continuous culture, control of the amount of production according to the market circumstances, and the like.

As microorganisms capable of producing polysaccharides, bacteria such as Agrobacter, Alcaligenes, Arthrobacter, Azotobacter, Bacillus, Pseudomonas and Klebsiella; yeasts such as Hansenula and Rhodotolura; and molds such as Pullularia, Rhizobium and Aspergillus are known. Investigations for the preparation of the polysaccharides by microorganisms have been continuously made since a few of them are applicable in the industries, and polysaccharides having new structures and properties are thus required.

To produce microbial polysaccharides, first of all, microorganisms having the desired characteristics are separated from nature, culture conditions to produce polysaccharides are studied with the separated strains, and then the studies must be made with regard to the purification of polysaccharides from culture medium, and their stability and applicability.

SUMMARY OF THE INVENTION

The present inventors have separated a novel microorganism capable of producing viscous polysaccharides from the soil, which have thermal stability and can reversibly form a gel by heat. It has been also found that polysaccharides produced by the separated microorganisms according to the invention have the above characteristics as well as the kind and constitution ratio of monosaccharides constituting a polysaccharide, which are different from those of known polysaccharides.

The object of the invention is to provide *Bacillus polymyxa* Haitai 1 capable of producing polysaccharides which have thermal stability and can reversibly form a gel by heat. Another object of the invention is to provide polysaccharides having the above characteristics which are produced by the said microorganisms.

The present invention is characterized by *Bacillus polymyxa* Haitai 1 which is separated from the culture medium comprising 2% starch and 1% soybean meal, and viscous polysaccharides produced by the above microorganisms which have thermal stability and can reversibly form a gel by heat. The strains of the invention are separated from the soil of a cabbage patch located Sootai-Ri, Daeso-Myun, Eumseong-Kun, Chungcheongbuk-Do, Republic of Korea.

BRIEF DESCRIPTION OF THE DRAWINGS

FIG. 2 is a graph showing the scanned results of solutions (0.0062 to 0.1%) having different concentrations of the roughly purified polysaccharide produced by *Bacillus polymyxa* Haitai 1 by a spectrophotometer at 190–370nm.

DETAILED DESCRIPTION OF THE INVENTION

*Bacillus polymyxa* Haitai 1 of the present invention has the following bacteriological properties:
(1) They have the ability to form spores.
(2) When cultivated in liquid, they produce the novel polysaccharides having the new structure which have thermal stability and can reversibly form a gel by heat.
(3) They produce polysaccharides having the above properties on agar plate.
(4) They grow in initial pH 3.3–7.9.

A normal medium comprising carbon source, nitrogen source and various mineral salts may be used as the medium of *Bacillus polymyxa* Haitai 1 characterized by the above properties. The carbon source may be carbohydrates such as glucose, galactose, mannose, fructose, xylose, sucrose, lactose, maltose, starch and so on. The nitrogen source may be an organic nitrogen such as corn steep liquor, peptone, yeast extract, dry yeast, soy sauce, soybean meal and so on. The mineral salts may be salts such as phosphate, calcium, manganese, sodium and so on.

The culture temperature of *Bacillus polymyxa* Haitai 1 according to the present invention is 10°–40° C., preferably 25°–37° C., and the initial pH of the culture medium is pH 3.3–7.9. As *Bacillus polymyxa* Haitai 1 is a facultative aerobic bacteria, it is preferable to supply plenty of oxygen in the culture.

The method for separating *Bacillus polymyxa* Haitai 1 is described in detail as follows:

About 2000 soil samples were collected throughout the country. A spoonful of the soil sample is charged into the sterilized test tube, and then treated at 80° C. for 30 min. After being suspended by the addition of 3 ml of physiological saline solution, the solution is applied to the agar medium plate comprising 2% starch, 1% soybean meal, 0.2% $KH_2PO_4$, 0.2% NaCl, 0.1% $MgSO_4.7H_2O$ and 0.2% $CaCl_2$. After being cultivated at 30° C. in the incubator for 2–3 days, the strains forming a viscous colony are primarily screened.

These strains are inoculated in the liquid medium described above, and then cultivated at 30° C. in a shaking incubator for 2–3 days. A viscous colony is collected and heated to 100° C. for 5 minutes, and then cooled to room temperature to screen a strain producing a viscous polysaccharide.

Figure 1A:
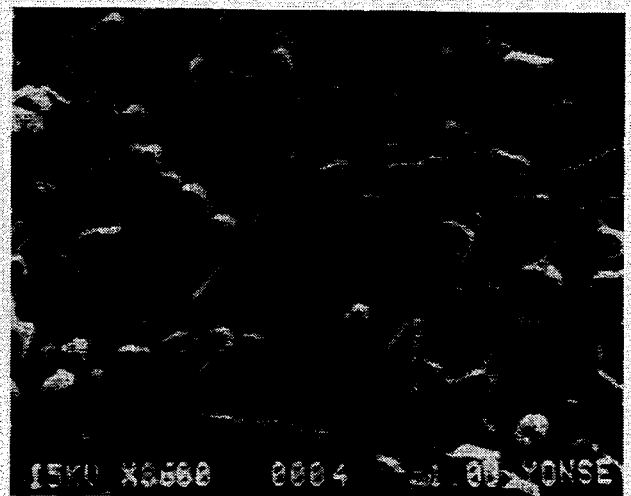
FIG. 1, (a) is a photograph of the external shape *Bacillus polymyxa* Haitai 1 by an electron microscope and (b) is a photograph of spore transection of the strain by a scan microscope.
Figure 1B:
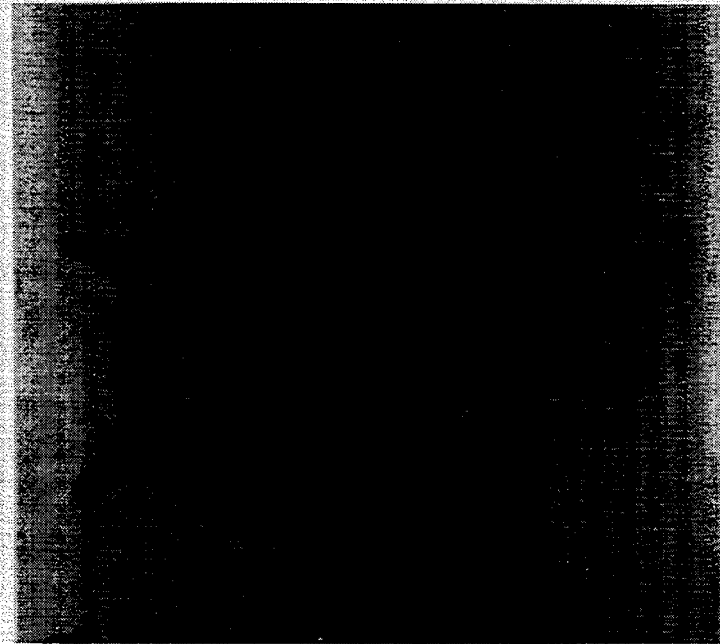

The bacteriological properties of the screened strain are as follows:
I. Morphology
1. The results observed by Microscope
   1) Vegetative cell: Bacillus
   2) Motility: yes
   3) Size: 0.7×3.2–3.8 μm
   4) Gram's stainability: Positive
   5) Spore: A star-like spore is formed since the spore coat is thick and forms the furrows (FIG. 1(*b*)).
2. Growing states in various culture media
   1) Nutrient agar (Difco) plate culture: the strains hardly grow.
   2) Nutrient broth (Difco) culture: the strains do not make a film on the top.
   3) Nutrient gelatin (Difco) culture: liquefaction is rapidly developed.
   4) Brain heart infusion (Difco) culture: growing states are good.
   5) Growing states in a culture medium including NaCl:
      0% - growth
      2% - growth
      5% - difficult
      7% - difficult
      10% - difficult II. Physiological properties
1. Growth temperature: 10°–40° C.
2. Optimum growth temperature: 27° C.
3. Growth pH: 3.3–7.9
4. Optimum growth pH: 7.4
5. Attitude to oxygen: facultative aerobic
6. Decomposition of starch: Positive
7. Decomposition of casein: Positive
8. Decomposition of dextran: Negative
9. Decomposition of cellulose: Positive
10. Decomposition of xanthan: Positive
11. Decomposition of mannan: Positive
12. Formation of indole: Negative
13. Methylred test: Negative
14. Catalase test: Positive
15. Oxidase test: Positive
16. Urease test: Negative
17. Formation of dihydroxyacetone: Positive
18. Decomposition of tyrosine: Negative
19. VP test: Negative
20. Formation of phenylalanine diaminase: Negative
21. Formation of lecithinase: Negative
22. Reduction test of nitrates: Positive
23. Hemolysis: Positive III. Fermentation of carbohydrates Each carbohydrate is added to the solution comprising 1% peptone, 0.2% $KH_2PO_4$, 0.2% NaCl, 0.05% $MgSO_4$, and 0.00625% Bromocrezol purple to provide a final concentration of 1%.

The reaction mixture is transferred to the test tube inserted Durham tube, sterilized, inoculated with the screened strain, and then observed to determine whether gas and an acid are formed in an incubator at 37° C. for 14 days.

The results are shown in the following table.

| Carbohydrates | Formation of acid | Formation of gas |
| --- | --- | --- |
| Arabinose | + | + |
| Cellobiose | + | + |
| Fructose | + | + |
| Galactose | + | + |
| Glucose | + | + |
| Glycerol | + | + |
| Inositol | − | − |
| Lactose | + | + |
| Maltose | + | + |
| Mannitol | + | + |
| Mannose | + | + |
| Melibiose | + | + |
| Raffinose | + | + |
| Salicine | + | + |
| Sorbitol | − | − |
| Sorbose | − | − |
| Starch | + | + |
| Sucrose | + | + |

| Carbohydrates | Formation of acid | Formation of gas |
|---|---|---|
| Xylose | + | + |

According to the above characteristics, the strain of the present invention is classified according to Bergey's Manual of Systematic Bacteriology (the 1st Ed (1986)). The separated strain is identified as *Bacillus polymyxa*. In light of the facts that the strain has a star-like spore and produces an acid and gas from glucose, the strain is presumed to be *Bacillus polymyxa*. However, taking into consideration that the strain strongly decomposes cellulose and grows below pH 5, the strain of the present invention is identified as a novel strain among *Bacillus polymyxa*. Accordingly, the strain has been named as *Bacillus polymyxa* Haitai 1, in which Haitai 1 means sub-species. Hence, the inventor has deposited with the international depository (under the Budapest Treaty on the International Recognition of the Deposit of Microorganisms for the Purposes of Patent Procedure), named "Korean Culture Center of Microorganisms" with the accession number of KCCM-10001 on Jul. 1, 1990.

A process for preparing the polysaccharides produced by the strain according to the present invention is described as follows: First, the strain is cultivated in the fermentation medium. The applicable medium may be a medium comprising a carbon source, a nitrogen source and mineral salts, suitable for growing the microorganisms. The carbon source needed for cultivation may be, for example, starch, mannose, lactose, maltose, glucose, fructose, galactose and so on. The nitrogen source may be, for example, corn steep liquor, peptone, dry yeast, soy sauce, soybean meal and so on, and the mineral salts may be phosphate, sodium, manganese, calcium salts and so on.

According to the present invention, the strain is cultivated at pH 5.5-6.5 at a temperature of 25°-37° C., generally for 2-3 days. During cultivation the strain is preferably supplied with air since the strain is a facultative aerobic bacteria.

The culture broth cultivated under the above conditions contains polysaccharides according to the present invention. The microorganisms and insoluble materials are removed in order to purify polysaccharides from the culture broth. For example, three volumes of water are added to the culture broth to decrease the viscosity, and then centrifuged to remove the microorganisms and insoluble materials. The solvent such as isopropyl alcohol is added thereto to precipitate polysaccharide. After being dried, the resulting precipitate is dissolved in water, and a solvent such as an isopropyl alcohol is also added to precipitate polysaccharides.

The above procedure is repeated several times, and the resulting precipitate is dried under vacuum to obtain the purified polysaccharide produced by the strain.

Figure 3:
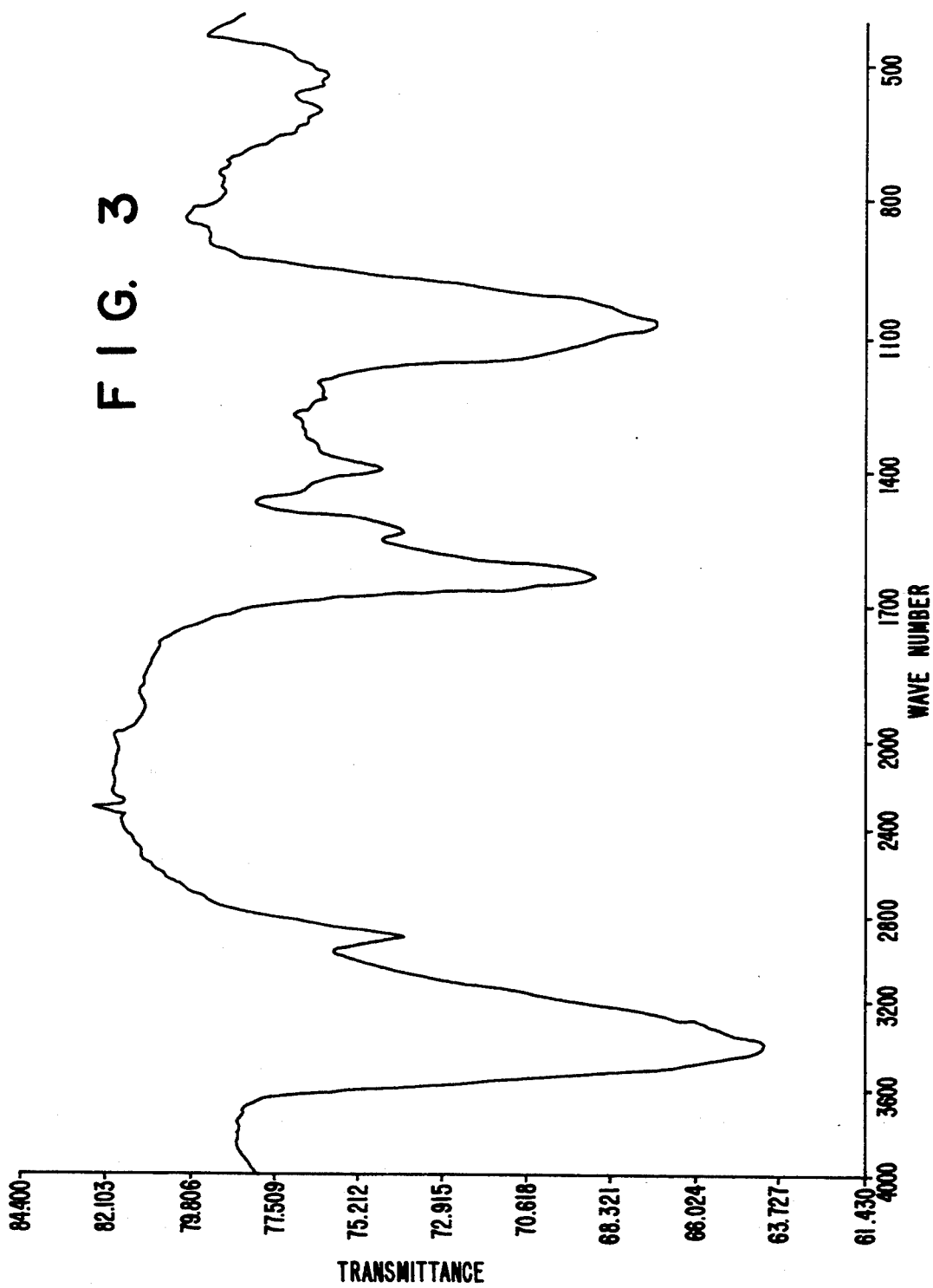
FIG. 3 is a graph of the IR spectrum of the polysaccharide shown in FIG. 2.
Figure 4:
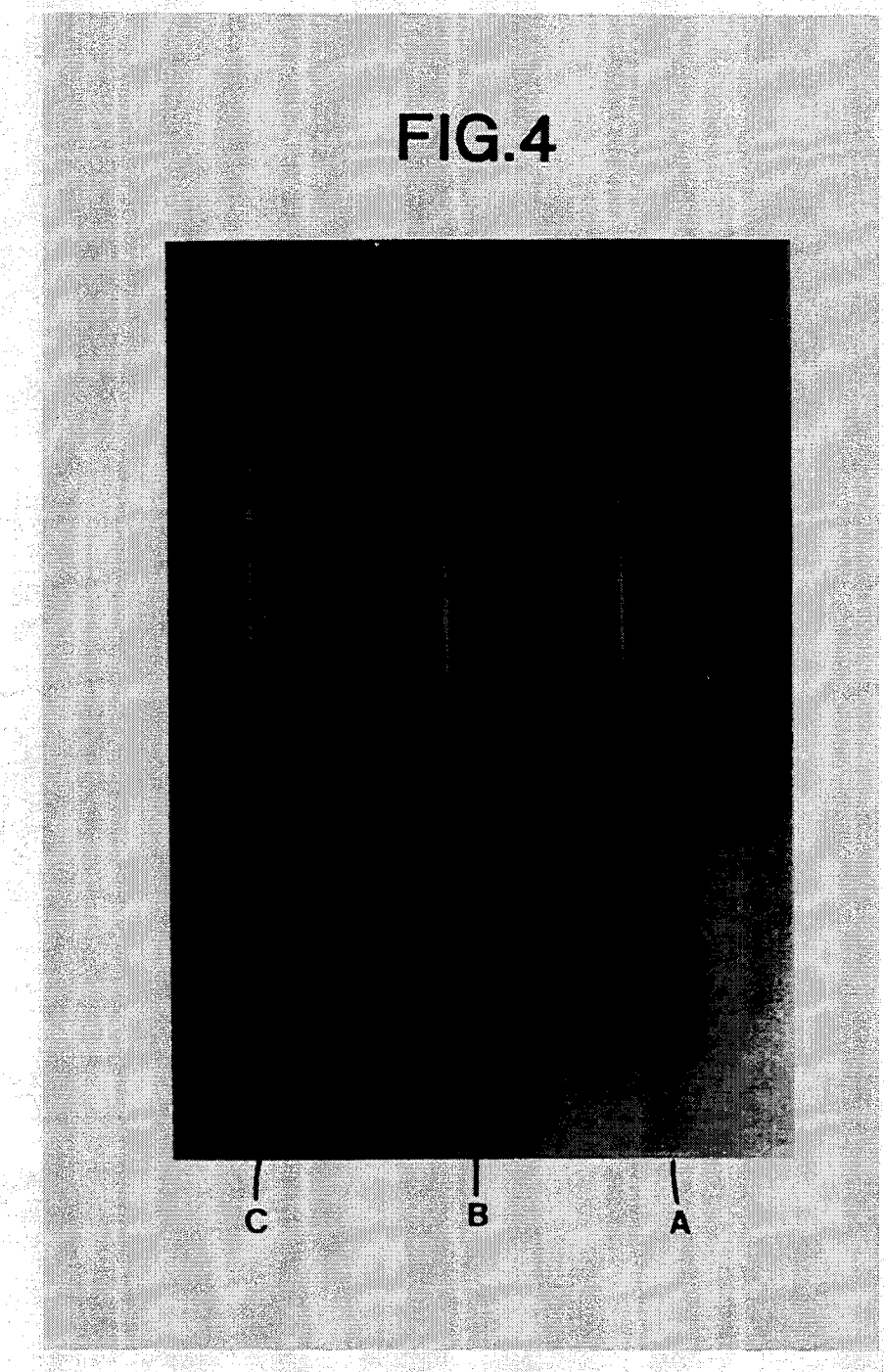
FIG. 4 is a photograph representing (A) a thermally treated culturing tube of *Bacillus polymyxa* Haitai 1, (B) a thermally untreated culturing tube of the same strain, and (C) the end of a culture tube which is loaded with the culture medium before inoculating the strain.
Figure 5:
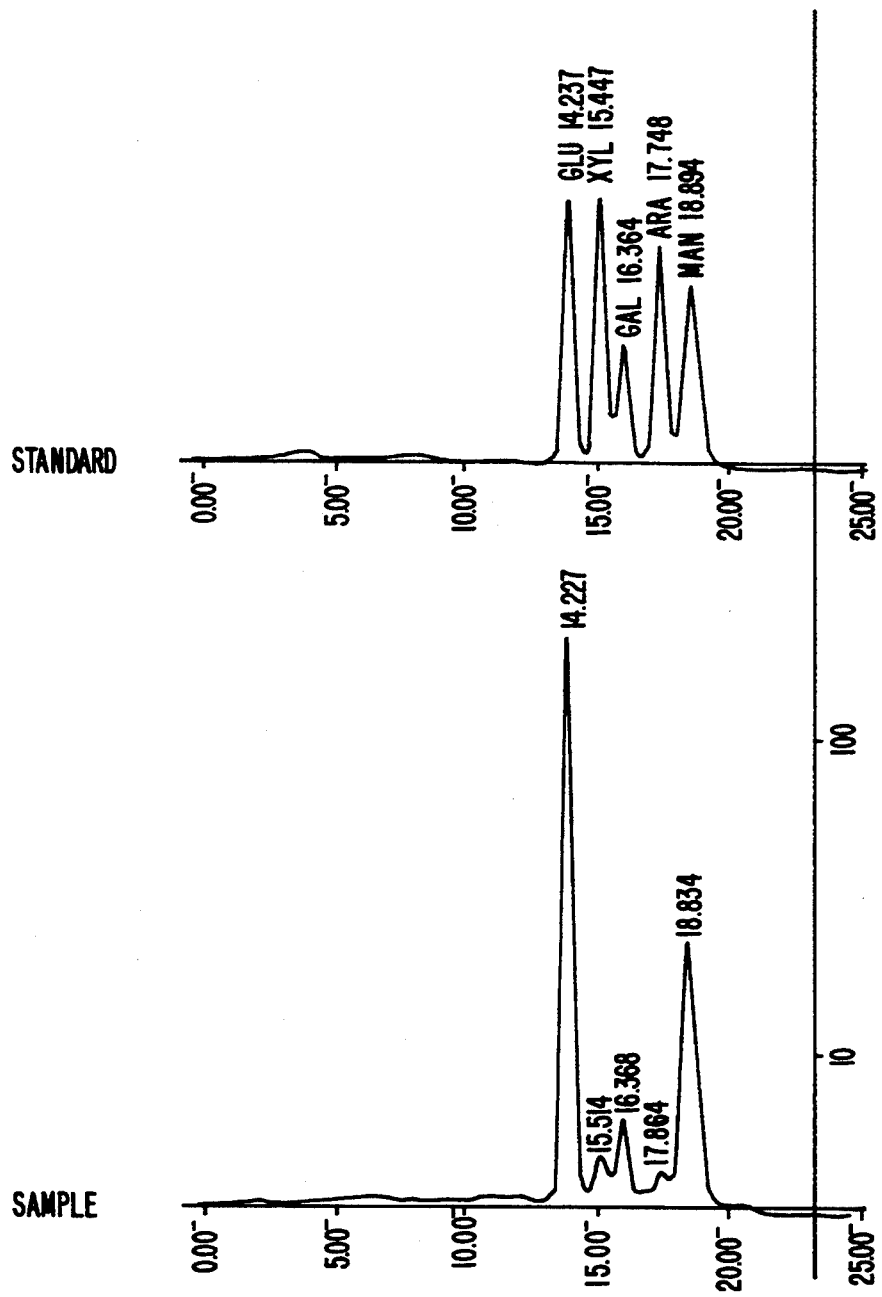
FIG. 5 is a graph representing the results of the analysis of the constituent sugars of the polysaccharide shown in FIG. 2 by HPLC, wherein the polysaccharide is hydrolyzed.

The results of the analysis of the polysaccharide obtained by the above method are as follows:
(1) Compositions
 crude protein: 10.06
 ash: 4.02
 crude lipid: 0.43
 carbohydrates: 85.49
(2) UV spectrum (FIG. 2)
 $\lambda_{max}$: 190 nm
(3) IR spectrum (FIG. 3)
(4) Solubility in a solvent soluble in water and insoluble in the organic solvent such as isopropyl alcohol, ethanol, methanol and acetone
(5) Color reaction
 Sulfate reaction (to carbohydrates): Positive
 Molish's reaction (to carbohydrates): Positive
 Reaction of 3% $FeCl_3$: Negative
 Iodide reaction: Negative
 Aniline—phthalate reaction: Negative
(6) Color of the material: white
(7) Viscosity
 1% solution of the polysaccharide is measured by SV-I cylinder of Haake viscometer at 16 rpm. When the polysaccharide solution is treated by heat, the viscosity is 2219mpa.s; the viscosity without treatment is 1253 mpa.s.
(8) Elemental analysis
 C:33.6%, H:4.98%, N:1.2%
(9) Thermal stability and Gel forming capacity (FIG. 4)
(10) Analysis of the constituent sugars 10 mg of the separated polysaccharide are dissolved in 1 ml of 2N $H_2O_4$, hydrolyzed at 100° C. for 6 hours and the obtained monosaccharides are then analyzed by HPLC (model-Waters). As a result, the constituent sugars are glucose, mannose, galactose, xylose and arabinose, and the molar ratio of these constituent sugars is 9.8:6.4:3.6:1.2:1.

The polysaccharide according to the present invention has the capacities of water holding, film forming and emulsifying in addition to the above characteristics. The polysaccharide of the present invention may be applied either alone or in combination with another polysaccharide to the food, cosmetic, oil and medicine industries.

The following Example further illustrates the present invention in detail.

EXAMPLE

Particular examples of the composition of the culture medium are specified in the following:
Composition of culture medium
1. Culture medium A
 2% starch, 1% soybean meal, 0.1% $KH_2PO_4$, 0.1% NaCl, 0.05% $MgSO_4.7H_2O$
 (sterilized at pH 5.8, 121° C. for 15 minutes in vapor pressure)
2. Culture medium B
 1% Trypton, 1% NaCl, 0.5% yeast extract
 (sterilized at pH 7.0, 121° C. in vapor pressure)

25 ml of medium B are placed in a 100 ml Erlenmeyer flask, inoculated with *Bacillus polymyxa* Haitai 1 and cultivated at 32° C. for 16 hours at 230 rpm. 25 ml of the above culture broth are inoculated in an Erlenmeyer flask including 175 ml of medium B and cultivated at 32° C. for 8 hours at 230 rpm. The culture broth is inoculated in a 7l fermentation tank containing 3.5 l of medium A, and then cultivated at 32° C. for 24 hours while the concentration of dissolved oxygen is maintained at 50% in the culture medium. 7 l of deionized distilled water are added to 3.5 l of the above culture broth. The solution is stirred at 40° C., and then centrifuged for 30 minutes at 8,000 rpm to remove the microorganisms. Isopropyl alcohol of five times is added to the supernatants to precipitate the polysaccharides. The precipitation by isopropyl alcohol is repeated three times, and the resulting precipitate is then dried under vacuum to obtain 22.43 g of the crude polysaccharide. The yield is 32%.

The obtained polysaccharide has the above characteristics. It is evident that the polysaccharide is composed of glucose, mannose, galactose, xylose and arabinose by an analysis of its constituent sugars.

What is claimed is:

1. An isolated microorganism of *Bacillus polymyxa* Haitai 1 having all of the identifying characteristics of KCCM-10001 which produces a polysaccharide which is viscous and thermally stable, and has the capacities of water holding, film forming and emulsifying, and reversibly forms a gel when heated.

2. A microorganism according to claim 1, wherein said polysaccharide comprises glucose, mannose, galactose, xylose and arabinose.

* * * * *

UNITED STATES PATENT AND TRADEMARK OFFICE
CERTIFICATE OF CORRECTION

PATENT NO. : 5,420,036
DATED : May 30, 1995
INVENTOR(S) : Ju Hyun YU et al.

It is certified that error appears in the above-indentified patent and that said Letters Patent is hereby corrected as shown below:

On the title page, item [54], Title should read

-- BACILLUS POLYMXYA HAITAI 1 CAPABLE OF PRODUCING POLYSACCHARIDES AND POLYSACCHARIDES PRODUCED BY THIS STRAIN --

Signed and Sealed this

Eighth Day of August, 1995

Attest:

BRUCE LEHMAN

*Attesting Officer*    *Commissioner of Patents and Trademarks*